(12) United States Patent
Mallet et al.

(10) Patent No.: US 11,357,816 B2
(45) Date of Patent: Jun. 14, 2022

(54) LIGAND CONTROLING INTERACTION BETWEEN GAGS WITH THEIR EFFECTOR MOLECULES AND USE THEREOF

(71) Applicants: CENTRE NATIONAL DE LA RECHERCHE SCIENTIFIQUE (CNRS), Paris (FR); INSTITUT NATIONAL DE LA SANTE ET DE LA RECHERCHE MEDICALE (INSERM), Paris (FR); SORBONNE UNIVERSITE, Paris (FR); ECOLE NORMALE SUPERIEURE, Paris (FR); COLLEGE DE FRANCE, Paris (FR)

(72) Inventors: Jean-Maurice Mallet, Vitry (FR); Solange Lavielle, Paris (FR); Rodrigue Marquant, Moulin sous Jouvent (FR); Alain Prochiantz, Paris (FR); Ariel Di Nardo, Palaiseau (FR); Damien Testa, Paris (FR)

(73) Assignees: CENTRE NATIONAL DE LA RECHERCHE SCIENTIFIQUE (CNRS), Paris (FR); INSTITUT NATIONAL DE LA SANTE ET DE LA RECHERCHE MEDICALE (INSERM), Paris (FR); SORBONNE UNIVERSITE, Paris (FR); ECOLE NORMALE SUPERIEURE, Paris (FR); COLLEGE DE FRANCE, Paris (FR)

(*) Notice: Subject to any disclaimer, the term of this patent is extended or adjusted under 35 U.S.C. 154(b) by 0 days.

(21) Appl. No.: 17/252,573

(22) PCT Filed: Jun. 17, 2019

(86) PCT No.: PCT/EP2019/065911
§ 371 (c)(1),
(2) Date: Dec. 15, 2020

(87) PCT Pub. No.: WO2019/243272
PCT Pub. Date: Dec. 26, 2019

(65) Prior Publication Data
US 2021/0252101 A1    Aug. 19, 2021

(30) Foreign Application Priority Data

Jun. 18, 2018  (EP) ................................. 18305752

(51) Int. Cl.
*A61K 38/00* (2006.01)
*A61K 38/04* (2006.01)
*C07K 14/47* (2006.01)

(52) U.S. Cl.
CPC .......... *A61K 38/04* (2013.01); *C07K 14/4725* (2013.01)

(58) Field of Classification Search
CPC ........................... A61K 34/04; C07K 14/4725
See application file for complete search history.

(56) References Cited

FOREIGN PATENT DOCUMENTS

WO    2011/029931 A1    9/2011

OTHER PUBLICATIONS

Beurdeley et al., "Otx2 binding to perineuronal nets persistently regulates plasticity in the mature visual cortex", The Journal of Neuroscience, vo. 32, No. 27, Jul. 4, 2012, pp. 9429-9437.
Hhc Lee et al. "Genetic Otx2 mis-location delays critical period plasticity across brain region", Molecular Psychiatry, vol. 22, Feb. 14, 2017, pp. 680-688.
Winter et al., "The Chemorepulsive Protein Semaphorin 3A and Perineuronal Net-Mediated Plasticity," 2016, Neural Plast., 3679545).
Miyata et al., "Persistent cortical plasticity by upregulation of chondroitin 6-sulfation," 2012, Nat Neurosci ., 15, 414-422.
Gunnar Dick et al. "Semaphorin 3A Binds to the Perineuronal Nets via Chondroit in Sulfate Type E Motifs in Rodent Brains", Journal of Biological Chemistry, vol. 288, No. 38, Aug. 12, 2013, pp. 27384-27395.

*Primary Examiner* — Jeanette M Lieb
(74) *Attorney, Agent, or Firm* — Arrigo, Lee, Guttman & Mouta-Bellum LLP

(57) ABSTRACT

The invention relates to new compounds that mimic Glycosaminoglycans and are able to control interaction between Glycosaminoglycans with their effector molecules. The compounds of the invention are peptides and are able to prevent or reduce the binding of at least one effector molecule with at least one glycosaminoglycan. The compounds according to the invention can be used as drug, in particular for the stimulation of the neurogenesis and more generally to treat nervous system related pathologies.

20 Claims, 4 Drawing Sheets

(EC'C'A) repeat (EC'AC') repeat

Figure 1:
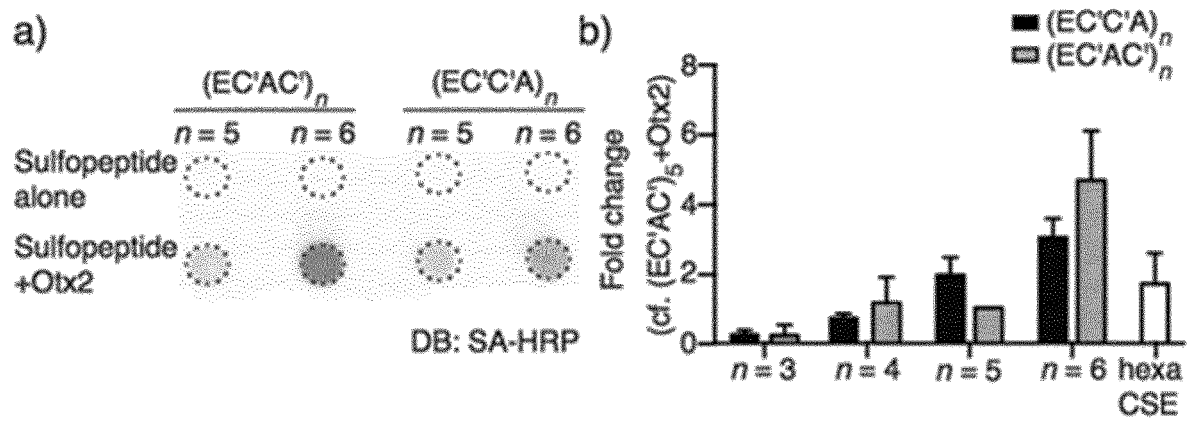

LIGAND CONTROLLING INTERACTION BETWEEN GAGS WITH THEIR EFFECTOR MOLECULES AND USE THEREOF

Glycosaminoglycans (GAG) are naturally-occurring carbohydrate-based molecules implicated in regulation of a number of cellular processes, including blood coagulation, angiogenesis, tumour growth, nerve cell development, smooth muscle cell proliferation, and gene expression, most likely by interaction with effector molecules such as cytokines, growth factors, serpins, etc.

GAG's are linear, non-branched chains of repeating two-sugar (disaccharide) units which may be up to 150 units in length, and are well known and described in the art. GAG's are often, but not always, found covalently bound to protein cores in structures called proteoglycans. Proteoglycan structures are abundant on cell surfaces and are associated with the extracellular matrix around cells.

Glycosaminoglycans can be divided into four main classes on the basis of the repeating disaccharide unit in the backbone. Typically, one sugar is a uronic acid, and the other is either an N-acetylglucosamine or an N-acetylgalactosamine. The classes are exemplified by the following four GAGs: (1) heparan sulfate (D-glucuronic acid/N-acetyl- or N-sulfo-D-glucosamine); (2) chondroitin/dermatan sulfate (D-glucuronic acid or L-iduronic acid/N-acetyl-D-glactosamine); (3) keratan sulfate (D-galactose/N-acetyl-D-glucosamine), and (4) hyaluronic acid. All GAG's, with the exception of hyaluronic acid, contain sulfate groups variously esterified to the ring hydroxyl groups of the sugars. These negatively charged groups are believed to figure prominently in the biological properties attributed to glycosaminoglycans. The naturally-occurring forms of GAG's, particularly heparin, heparan sulfate, chondroitin sulfate and dermatan sulfate, in fact are complex hetero-oligosaccharides composed of mixtures of differentially sulfated sugar residues. For example, chondroitin sulfate (CS) is the most abundant glycosaminoglycan (GAG) in the central nervous system (CNS) matrix (Djerbal et al., 2017, Glycoconj. 34, 363-376) and consists of a protein backbone to which is linked chains containing hundreds of disaccharide repeats.

A fascinating characteristic of GAGs is that their polysaccharide units are modified through epimerisation, N- and O-sulfation, and deacetylation, and thus can be finely tuned for interactions.

For example, it has been shown during postnatal brain development that specific sulfation patterns are crucial for the timing of critical periods during which a given neural circuit is highly plastic. As used herein, the term "critical period" refers to a time period during the development of an organism in which the organism's nervous system is able to acquire a specific functional ability and/or structural configuration, typically at least in part in response to external environmental stimuli. The timing and duration of the critical period may depend upon the environmental stimuli received. For example, lack of certain environmental stimuli prolongs the critical period. These critical periods are remodeling neuronal connectivity and are essential for adapting to the environment and for learning and behavior.

These critical periods are closely related to nervous system plasticity. As used herein, the term "plasticity" refers to the capacity of the nervous system, or a portion thereof, to change (e.g., to reorganize) its structure and/or function, generally in response to an environmental condition, injury, experience, or ongoing nervous system activity. Plasticity may involve the proliferation, growth or movement of neurons or glial cells. Plasticity may involve formation of new synaptic connections between neurons and/or strengthening or weakening of existing synaptic connections. Plasticity may involve neurogenesis.

These critical periods are known to be present in sensory systems such as binocular vision in the visual cortex or tonotopic map refinement in auditory cortex. They are also present in motor systems and even areas of higher cognitions in the brain such as human language acquisition.

These critical periods arise for example from the maturation of cortical inhibitory GABAergic Parvalbumin neurons (PV cells) driven by Orthodenticle homeobox protein 2 (Otx2) homeoprotein transcription factor. Otx2 is synthesized outside the cerebral cortex, transported in the extracellular milieu, and internalized specifically by PV cells. This internalization specificity is mediated by disulfated chondroitin sulfate (type D (CS-D) or type E (CS-E)) contained within as specialized extracellular matrix called perineuronal net (PNN).

After this critical periods closure, PV cells remain mature and intrinsic potential for plasticity is actively dampened resulting in the stabilization of brain circuits, which is accompanied by the formation of perineuronal nets (PNNs) around maturing PV cells.

It has further been shown that the critical periods during which a given neural circuit is highly plastic appear to be altered in several neurological and psychiatric diseases including for example epilepsy, schizophrenia, depression, autism and Alzheimer's disease.

Moreover, a GAG-binding motif (RKQRRER) was discovered in the primary sequence of Otx2, revealing interactions between Otx2 and glycosaminoglycans (e.g. disulfated chondroitin sulfate) contained within PNNs surrounding PV cells. Beurdeley et al., (2012, J. Neurosci., 32, 9429-37) have further shown that cortical infusion of a peptide containing this "RK" motif competes with Otx2 for GAG binding, depleting mature PV cells of their Otx2 content, restoring visual cortical plasticity in mature mice and rescuing cortical acuity in amblyopic mice.

Lee et al.,(2017, Mol. Psychiatry, 22, 680-688) have shown that Otx2 is involved not only in visual, but also auditory plasticity.

Winter et al., (2016, Neural Plast., 3679545) have shown that controlled neutralization of Sema3A in PNN may be an important approach to enhance neuronal plasticity and functional repair after injury.

Miyata et al., 2012, Nat Neurosci., 15, 414-422 and Dick et al., 2013, J Biol Chem, 288, 27384-95 have shown that Otx2 and Semaphorin-3A (Sema-3A) are both keys actors of visual cortex plasticity and share similar motif for binding disulfated chondroitin sulfate type E (CS-E) (RKQRRER and RKQRRQR, respectively).

The Inventors thus concluded that critical periods and associated plasticity timing is controlled in part by the interaction of GAGs with its effector molecule, e.g. Otx2 or Semaphorin, and propose to interfere with said interaction to provide an approach to modify the critical periods timing, more particularly to modify the plasticity of the nervous system, for research and therapeutic applications. It is thus necessary to provide compounds able to control interaction between GAGs with effector molecules.

Extraction of pure compounds from natural sources and chemical or enzymatic synthesis of GAG fragments remains difficult and inefficient. Efforts have been made to reduce the complexity of GAG structures and syntheses, showing for example that the interactions between proteins and GAGs are mainly electrostatic and that the most critical aspect is the correct space distribution of charges, but these results are still at the research level and do not allow to define compounds able to control interaction between GAGs with effector molecules.

Similarly, modified natural and synthetic polymers have been proposed as GAG surrogates (such as for example polyacrylate, poly 2-acrylamido-2-methylpropane sulfonic acid, poly(sodium-4-styrenesulfonate) (PSS), poly(vinyl sulfonate) (pVS), sulfated lignin derivatives, polyphenols, polyglycidol copolymers, poly(ethylene oxide)-bl-poly(propylene oxide)-bl-poly(ethylene oxide) (Pluronic F-127) with sulfate groups. While these strategies showed some success, they lack sequence modulations and show only non-specific electrostatic interactions with proteins. Alternatively, defined small molecules have been used as GAG mimics: sulfated aminosides, N-hetero-aroyl amino-saccharide, b-cyclodextrin sulfates, and aptamers.

Thus, there is still an important need in the art to develop new compounds and methods allowing to control interaction between GAGs with their effector molecules. More particularly, there is still a need for alternative approaches for modifying the plasticity of the nervous system, more particularly for modifying the critical periods timing of the nervous system plasticity.

Thus there is an important need in the art to develop compounds and methods able to modify the nervous system critical periods timing, more particularly able to modify the plasticity of the nervous system.

Similarly, there is a need in the art for improved treatments that would enhance recovery following damage to the CNS and/or help improve CNS and cognitive function in neuropsychiatric and neurodevelopmental disorders. More particularly, there is a need for new compounds and methods that play a role in key nervous system properties such as plasticity and that can be modulated to provide a therapeutic benefit.

According to the present invention, the inventors aimed to develop new compounds able to control interaction between GAGs with their effector molecules, more particularly new ligands that do not have the drawbacks of previously developed polymers.

According to a first embodiment, the present invention provides a ligand, or any of its pharmaceutically acceptable salt, said ligand comprising or consisting of a polypeptide of the general formula (I):

[X]$_n$     (I)

wherein
n is comprised between 3 and 50,
X is a peptide comprising from 4 to 6 amino acids,
X comprises an amino acid selected from the group consisting of glutamic acid and aspartic acid,
X comprises one or two cysteic acid (s), preferably two,
X comprises at least one neutral amino acid other than cysteine,
wherein said ligand is able to interact with binding of one effector molecule with at least one glycosaminoglycan (GAG).

In one embodiment, the said ligand is characterized in that n is comprised between 3 and 35, more particularly between 3 and 15, preferably between 3 and 6.

The compound of formula (I) can be in the form of its pharmaceutically acceptable salt. In particular the counter ion of the salt may be selected in the group consisting of metallic cations such as sodium, potassium, magnesium, calcium, ammonium or alkylammonium.

Cysteic acid is an amino sulfonic acid that is the sulfonic acid analogue of cysteine; i.e. it is an amino acid that has a C-terminal sulfonic acid group. Its synthesis is widely disclosed in the art, and the compound is commercially available.

Cystein is a natural α-amino acid characterized by the presence of a sulfhydryl —SH group forming a thiol. Cysteine is present in most proteins in small amounts. Its presence in proteins is very important since it allows the formation of disulfide bridges. The thiol group is very fragile because it oxidizes easily. Its oxidation leads to cystine, which consists of two molecules of cysteine linked by a disulfide bridge. A more energetic oxidant can oxidize cysteine by giving cysteic acid.

Homocysteine is a non-proteinogenic amino acid that is a result of the catabolism of methionine or cystathionine. The denomination of homocystein comes from its similarity with cysteine. Indeed, homocystein differs from cystein in that the later chain of homocystein contains two methyl groups while the lateral chain of cystein contain only one methyl group. The reactivity of the sulfhydryl is similar in cystein and homocystein.

According to one embodiment, the cysteic acid can be replaced by homocysteic acid and consequently X can comprise one or two amino acid(s), preferably two identical or different, selected in the group comprising cysteic acid and homocysteic acid.

In a further embodiment, the ligand is characterized in that X comprises two cysteic acids.

In another embodiment, the ligand is characterized in that X comprises two homocysteic acids.

In another embodiment, the ligand is characterized in that the "at least one neutral amino acid other than cysteine" is chosen from the group consisting of Alanin, Aspargin, Glutamin, Histidin, Isoleucin, Methionin, Phenylalanin, Prolin, Serin, Threonin, Tryptophan, Tyrosin, Valin and 2-aminoisobutyric acid.

Preferably, "the at least one neutral amino acid other than cysteine" is alanine, serine, threonine, and more preferably alanine It is also a preferred embodiment that the ligand is characterized in that the neutral amino acid other than cysteine is alanine.

Preferably, X comprises at least one and up to 2, preferably up to 3, more preferably up to 4 neutral amino acid other than cystein.

In another embodiment, the ligand of the invention is characterized in that the amino acid selected from the group consisting of glutamic acid and aspartic acid is placed in the first position of peptide X starting from the C-terminus.

In another preferred embodiment, the ligand of the invention is characterized in that the amino acid selected from the group consisting of glutamic acid and aspartic acid is glutamic acid.

According to special embodiment, the amino acid residues of the ligand of the invention can be D or L or a mixture of D and L.

According to special embodiment, the ligand of the invention is characterized in that X is the same or different. This means that the "n" repetition of the motif "X" can comprise a repetition of several identical peptide motifs or several different peptide motifs, of mixture thereof. Different means that at least one motif X can be different from the other ones. Different means differing in the nature and quantity of amino acids.

According to another embodiment, the ligand is characterized in that X is identical. This means that the ligand comprises the repetitions, from 3 to 50 times, more particularly from 3 to 15 times, preferably from 3 to 6 times of an identical peptide motif X.

In a preferred embodiment, the ligand according to the invention is characterized in that X is a peptide comprising 4 amino acids.

In a particular embodiment the ligand is characterized in that it is synthetic and non-natural.

According to preferred embodiment, X in polypeptide $[X]_n$ is selected in the group consisting of EACC, ECCA and ECAC, with C is cysteic acid, A is alanine, E is glutamic acid.

According to preferred embodiment, amino acids are in L-from.

In a preferred embodiment the ligand according to the invention is comprising or consisting of polypeptide $[X]_n$ selected in the group consisting of $(EACC)_n$, $(ECCA)_n$, $(ECAC)_n$.

According to preferred embodiment, amino acid are in L-from.

According to preferred embodiment, n is from 3 to 6, more preferably n is 5 or 6, even more preferably n is 6.

In even more preferred embodiment, the ligand according to the invention is comprising or consisting of polypeptide $[X]_n$ selected in the group consisting of $(ECCA)_n$ or $(ECAC)_n$.

In even more preferred embodiment, the ligand according to the invention is comprising or consisting of polypeptide $[X]_n$ selected in the group consisting of $(ECCA)_n$ or $(ECAC)_n$, with n is comprised between 3 and 6, particularly n is 5 or 6, even more preferably n is 6.

According to the invention, the polypeptide $[X]_n$ can be linear or dendritic.

According to one special embodiment, the polypeptide $[X]_n$ according to the invention is linear. Linear means that the polypeptide comprises a succession of [X] moieties repeated according to a continuous chain of amino acids linked by a peptide bond.

According to another special embodiment, the polypeptide $[X]_n$ according to the invention is dendritic and [X] moieties, more particularly (ECCA) or (ECAC) moieties, are grafted on a polylysine core chain, $K_p$ as described below.

Peptide dendrimers are radial or wedge-like molecules, of high molecular weight, that comprise basic amino acids linked through peptide or amide bonds that are found both inside the branching core and on the outer surface. This gives a "hairy" presentation of ligand favoring multivalent interactions (e.g. two ligand chains, one protein), which may be more pertinent for affinity and specificity in vivo.

Accordingly the polypeptide may then be in the form of a comb, wherein a principal branching core is grafted with the polypeptide $[X]_n$. Preferably the branching core is a polylysine core chain $(K)_p$; wherein K is Lys and p is comprised between 3 and 8, preferably between 3 and 5, particularly 4; and is grafted with the polypeptide $[X]_n$.

As used herein, the term "ligand is able to interact with binding of one effector molecule with at least one glycosaminoglycan (GAG)" means that the ligand of the invention is able to prevent or reduce the binding of at least one effector molecule with at least one glycosaminoglycan (GAG).

According to one preferred embodiment, the ligand of the Invention is able to prevent the binding of at least one effector molecule with at least one glycosaminoglycan (GAG).

According to another preferred embodiment, the ligand of the Invention is able to reduce the binding of at least one effector molecule with at least one glycosaminoglycan (GAG).

According to preferred embodiment, the ligand of the Invention is able to bind to at least one effector molecule.

According to preferred embodiment, the said effector molecule is a protein comprising a glycosaminoglycan binding site. In the present application, the expression "glycosaminoglycan binding site" means region of the said protein that interact strongly with glycosaminoglycan GAG (particularly GAG consisting of heparan sulfate, heparin or chondroitin sulfate). This binding pocket is generally fitted from basic side chains of the protein, and contains BBXB motif where X is a hydrophilic residue and B is selected in the group consisting of Arginine and Lysine. The identification of the glycosaminoglycan binding site can be achieved by a skilled person according to technical means known such as protein sequence analysis, X rays and NMR structure determinations. In particular a "glycosaminoglycan binding site" can be RKQRRER or RKQRRQR.

According to one preferred embodiment, the ligand of the Invention is able to interact with a glycosaminoglycan (GAG) binding site.

According to another preferred embodiment, the ligand of the Invention is able to mimic glycosaminoglycan (GAG) binding.

According to one preferred embodiment, the ligand of the Invention is able to prevent the binding of at least one glycosaminoglycan (GAG) to a glycosaminoglycan binding site.

According to another preferred embodiment, the ligand of the Invention is able to reduce the binding of at least one glycosaminoglycan (GAG) to a glycosaminoglycan binding site.

According to preferred embodiment, the said glycosaminoglycan GAG is selected in the group consisting of heparan sulfate, heparin and chondroitin sulfate.

In a preferred embodiment, the said effector molecule is selected from the group consisting of transcription factors, growth factors, signaling factors, coagulation cascade proteins.

In a preferred embodiment, the said effector molecule is chosen from the group consisting of Semaphorins, homeoprotein family, and preferably it is Otx2 or Semaphorin-3A.

According to one preferred embodiment, the ligand according to the invention is comprising or consisting of polypeptide $[X]_n$ selected in the group consisting of $(ECAC)_5$, $(ECAC)_6$ and $(ECCA)_5$ and $(ECCA)_6$ and the said effector molecule is homeoprotein family, and preferably is Otx2.

According to another preferred embodiment, the ligand according to the invention is comprising or consisting of polypeptide $[X]_n$ selected in the group consisting of $(ECAC)_5$ and $(ECAC)_6$ and the said effector molecule is Semaphorins, and preferably is Semaphorin-3A.

The polypeptide $[X]_n$ comprised is the ligand according to the invention can be manufactured according to usual and well known techniques. Synthesis route can use Fmoc strategy on a Rink amide MBHA resin as known in the art. A 6-aminohexanoic acid (Ahx) spacer can be introduced at the N-terminus and the peptidyl resins can either acetylated (Ac) or acylated with a biotin sulfone (Biot(SO2)).

The peptides can be cleaved from the resin by TFA and precipitated in diethyl ether to give either Ac-Ahx-(X)n-NH2, Ac-Ahx-(X)n-NH2, Biot(SO2)-Ahx-(X)n-NH2, or Biot(SO2)-Ahx-(X)n-NH2. These precursors can be oxidized with performic acid to give cysteic acid peptides, then neutralized with aqueous ammonia resulting in GAG mimics peptides according to the invention with either an acetyl or a biotin sulfone at the N-terminus and an amide at the C-terminus. Crude sulfopeptides can be desalted on Sephadex G25 and purified, for example by reverse phase HPLC and characterized by mass spectroscopy. These GAG mimic peptides can be stored for months at −20° C. as sodium salts.

It is also an object of the present invention to provide a ligand as described above according to any previous embodiment for its use as a medicament.

The present invention further concerns a composition comprising at least one ligand as defined above, and a pharmaceutically acceptable excipient.

As used herein, the term "pharmaceutically acceptable" refers to excipient that do not produce an adverse, allergic or other unwanted reaction when administered to an animal, or human, as appropriate. As used herein, "pharmaceutically acceptable excipient" includes any and all solvents, dispersion media, coatings, antibacterial and antifungal agents, isotonic and absorption delaying agents and the like. The use of such excipient for pharmaceutical active substances is well known in the art.

The composition of the invention is suitably buffered in order to be appropriate for human use at a physiological or slightly basic pH (e.g. from approximately pH 7 to approximately pH 9). Suitable buffers include without limitation phosphate buffer (e.g. PBS), bicarbonate buffer, HEPES and PIPES buffers and/or Tris buffer. The composition of the invention can further comprise a diluent appropriate for human or animal use. It is preferably isotonic, hypotonic or weakly hypertonic and has a relatively low ionic strength. Representative examples include sterile water, physiological saline (e.g. sodium chloride), Ringer's solution, glucose, trehalose or saccharose solutions, Hank's solution, and other aqueous physiologically balanced salt solutions (see for example the most current edition of Remington: The Science and Practice of Pharmacy, A. Gennaro, Lippincott, Williams & Wilkins). Pharmaceutically acceptable vehicles included in the composition of the invention must also allow the preservation of its stability under the conditions of manufacture and long-term storage (i.e. at least one month with a preference for at least one year) at freezing (e.g. −70 deg. C., −20 deg. C.), refrigerated (e.g. 4 deg. C.) or ambient temperatures. Additional pharmaceutically acceptable excipients may be used for providing desirable properties, including for example modifying or maintaining the pH, osmolarity, viscosity, clarity, colour, sterility, stability, rate of dissolution of the formulation, modifying or maintaining release or absorption into an the human or animal organism, promoting transport across the blood barrier or penetration in a particular organ (e.g. brain).

A composition comprising any one of the ligand described herein may be formulated for sustained or slow release (also called timed release or controlled release). Such compositions may generally be prepared using well-known technology and administered by, for example, oral, rectal, intradermal, intranasal, or subcutaneous implantation, or by implantation at the desired target site. Sustained-release formulations may contain the compound dispersed in a carrier matrix and/or contained within a reservoir surrounded by a rate controlling membrane.

The present invention further concerns a ligand or composition according to any previous embodiment for its use as a plasticity-modifying agent.

As used herein, the term "plasticity-modifying agent" refers to a substance or composition whose administration to a subject, either alone or in combination with one or more other substances or non-pharmacological therapy, results in a detectable modification in the plasticity of at least a portion of the nervous system. The modification may be evidenced by a modification in nervous system function and/or structure as compared with the function and/or structure that would be observed in the absence of the agent.

According to preferred embodiment, the plasticity-modifying agent is able to reopen critical period (e.g. the plasticity-modifying agent of the invention is able to initiate critical period and/or to control critical period timing and duration). According to another preferred embodiment, the plasticity-modifying agent is able to initiate plasticity in nervous system, or a portion thereof, and to change (e.g., to reorganize) structure and/or function of the said nervous system, or a portion thereof. According to another preferred embodiment, the plasticity-modifying agent is able to stimulate neurogenesis.

The present invention further concerns a method for modifying plasticity in the nervous system, or a portion thereof, in a subject in need, comprising the steps of administering a plasticity-modifying agent in an amount effective to modify nervous system plasticity, wherein the plasticity-modifying agent is a ligand or composition according to the present invention and interacts with binding of one effector molecule with at least one glycosaminoglycan (GAG) in nervous system, or a portion thereof, of said subject in need.

The present invention further concerns a method for modifying plasticity in the nervous system, or a portion thereof, in a subject in need, comprising the step of administering a plasticity-modifying agent in an amount effective to modify nervous system plasticity, wherein the plasticity-modifying agent is a ligand or composition according to the present invention and prevents or reduces the binding of one effector molecule with at least one glycosaminoglycan (GAG) in nervous system, or a portion thereof, of said subject in need.

The invention further provides methods of promoting reorganization or recovery in the nervous system, or a portion thereof, of a subject comprising step of administering a plasticity-modifying agent to a subject in need thereof, wherein the agent is administered either alone or in combination with one or more additional agents in an amount effective to promote nervous system reorganization or recovery, wherein the plasticity-modifying agent is a ligand or composition according to the present invention and interacts with binding of one effector molecule with at least one glycosaminoglycan (GAG) in nervous system, or a portion thereof, of said subject in need.

The invention further provides methods of promoting reorganization or recovery in the nervous system, or a portion thereof, of a subject comprising step of administering a plasticity-modifying agent to a subject in need thereof, wherein the agent is administered either alone or in combination with one or more additional agents in an amount effective to promote nervous system reorganization or recovery, wherein the plasticity-modifying agent is a ligand or composition according to the present invention and prevents or reduces the binding of one effector molecule with at least one glycosaminoglycan (GAG) in nervous system, or a portion thereof, of said subject in need.

The plasticity-modifying agent may contribute to (e.g., enhance) recovery or reorganization in the subject's nervous system and/or promote normalization of function. In other words, the degree of reorganization or recovery of the nervous system, or improvement of function, is greater than would have been the case if the agent had not been administered to the subject.

The present invention further concerns a method for stimulating neurogenesis in the nervous system, or a portion thereof, in a subject in need, comprising the steps of administering a plasticity-modifying agent in an amount effective to stimulate neurogenesis, wherein the plasticity-modifying agent is a ligand or composition according to the present invention and interacts with binding of one effector molecule with at least one glycosaminoglycan (GAG) in nervous system, or a portion thereof, of said subject in need.

The present invention further concerns a method for stimulating neurogenesis in the nervous system, or a portion thereof, in a subject in need, comprising the step of administering a plasticity-modifying agent in an amount effective to stimulate neurogenesis, wherein the plasticity-modifying agent is a ligand or composition according to the present invention and prevents or reduces the binding of one effector molecule with at least one glycosaminoglycan (GAG) in nervous system, or a portion thereof, of said subject in need.

The plasticity-modifying agent may contribute to stimulate neurogenesis in the subject's nervous system. In other words, the degree of neurogenesis is greater than would have been the case if the agent had not been administered to the subject.

According to preferred embodiment, in such methods the said effector molecule is a protein comprising a glycosaminoglycan binding site.

According to preferred embodiment, in such methods the said glycosaminoglycan GAG is selected in the group consisting of heparan sulfate, heparin and chondroitin sulfate.

In a preferred embodiment, in such methods the said effector molecule is selected from the group consisting of transcription factors, growth factors, signaling factors, coagulation cascade proteins.

In a preferred embodiment, in such methods the said effector molecule is chosen from the group consisting of Semaphorins, homeoprotein family, and preferably it is Otx2 or Semaphorin-3A.

According to special embodiment, "nervous system, or a portion thereof" designates the "central nervous system" (CNS) which includes the brain, spinal cord, optic, olfactory, and auditory systems. The CNS comprises both neurons and glial cells (neuroglia), which are support cells that aid the function of neurons. Oligodendrocytes, astrocytes, and microglia are glial cells within the CNS. The portion of the nervous system may be any functionally or structurally defined part, area, region, unit, or component of the nervous system (which terms are used interchangeably herein). Portions of the nervous system include cortex, cerebellum, thalamus, hypothalamus, hippocampus, amygdala, basal ganglia (caudate nucleus, putamen and globus pallidus), midbrain, pons, medulla, nerve tracts, etc., and any subportion of the foregoing. For example, subregions of the cortex include visual cortex, auditory cortex, somatosensory cortex, entorhinal cortex, olfactory cortex, etc. It will be appreciated that these regions themselves may be composed of smaller subregions.

As used herein, the term "recovery" refers to the process in which a nervous system or part thereof that has at least in part lost the ability to perform a function that it previously performed, regains at least in part the ability to perform the function.

The term "reorganization," as used in reference to the nervous system or a portion thereof, refers to the process in which a portion of the nervous system wholly or partially assumes, i.e., takes on, a function (e.g., a sensory, motor, or cognitive function) that was not previously performed by that portion of the nervous system. The function or task may, but need not have been, previously performed by a different portion of the nervous system. Functional reorganization may, but need not, entail one or more aspects of structural reorganization. Functional reorganization may also be referred to as functional rearrangement.

According to another embodiment, there is a need to develop non-invasive approaches that target specific proteins within the choroid plexus. Through secretion of CSF, the choroid plexus is important for brain homeostasis and delivers signals, including Otx2, that are implicated in brain development, neurogenesis and plasticity.

According to one special embodiment, the invention relates to the use of a ligand according to the invention to treat a patient in need thereof by the alteration of choroid plexus function.

In a preferred embodiment the ligand of the Invention is an anti-Otx2 compounds active in the intracellular space of choroid plexus cells.

In a preferred embodiment the ligand of the Invention is able to sequester Otx2 in the extracellular milieu and thus can alter ocular dominance plasticity.

As used herein, the term "subject" refers to an individual to whom an agent is to be delivered. Preferred subjects are mammals, particularly primates or humans.

According to special embodiment, the said subject in need is suffering of disease and/or neurological conditions and/or nervous system damage, more particularly disease and/or neurological conditions and/or nervous system damage requiring stimulation of the neuronal plasticity. According to special embodiment, said diseases and/or neurological conditions and/or nervous system damage is regulated by Otx2 or Sema 3A.

According to special embodiment, said disease and/or neurological conditions and/or nervous system damage is selected from the group comprising:

nervous system damage following for example cerebrovascular accident, ischemic, hemorrhagic, neoplastic, degenerative, traumatic, and/or neurodevelopmental damage;

nervous system damage following events such as stroke or injury (e.g., due to accident or surgery);

diseases and conditions including, but not limited to, neurodegenerative diseases such as multiple sclerosis, amyotrophic lateral sclerosis, subacute sclerosing panencephalitis, Parkinson's disease, Huntington's disease, muscular dystrophy, Alzheimer's disease, idiopathic dystonia, Spinal muscular atrophy or Wilson's disease;

conditions caused by nutrient deprivation or toxins (e.g., neurotoxins, drugs of abuse);

neurodevelopmental diseases such as autism or dyslexia, i.e., diseases in which at least a portion of the nervous system fails to develop normal structure and/or function;

neuropsychiatric diseases such as schizophrenia and bipolar disorders, i.e., diseases in which at least a portion of the nervous system fails to achieve its typical level of cognitive function;

depression, epilepsy;

degenerative diseases affecting the eyes or ears (i.e., the vision or audition) such as glaucoma or amblyopia, for example.

As used herein, an "effective amount" of a plasticity-modifying agent refers to the amount of the plasticity-modifying agent sufficient to elicit a desired biological response. As will be appreciated by those of ordinary skill in this art, the absolute amount of a particular plasticity-modifying agent that is effective may vary depending on such factors as the desired biological endpoint, the agent to be delivered, the target tissue, etc. Those of ordinary skill in the art will further understand that an "effective amount" may be administered in a single dose, or may be achieved by administration of multiple doses. A desired biological response may be, for example, (i) functional or structural reorganization of synaptic connections, dendrites, or axon projections; (ii) maintenance of synaptic connections, dendrites, or axon projections under conditions in which they would otherwise deteriorate; (iii) regeneration of a nerve or an axonal projection system or its maintenance under conditions in which it would otherwise deteriorate; (iv) an improvement in performance of a task requiring motor or sensory function; (v) an improvement in performance of a task requiring cognitive function, e.g., improved performance on a test that measures learning and/or memory; (vi) a slowing in the rate of decline in motor, sensory, and/or cognitive function.

As used herein, the term "function," with reference to the nervous system or a part thereof, is used broadly herein to refer to any function, role, task, or activity performed by the nervous system or a component thereof. The term includes, without limitation, the ability to process and recall information, regulate behavior, stimulate release of endogenous chemicals, control motor functions, receive and process sensory input, maintain consciousness, etc.

The dose of plasticity-modifying agent to be administered according to the Invention may depend upon the subject's condition, that is, stage of the disease and/or neurological conditions and/or nervous system damage, severity of symptoms caused by the disease and/or neurological conditions and/or nervous system damage, general health status, as well as age, gender, and weight, and other factors apparent to a person skilled in the medical art. Plasticity-modifying agent may be administered in a manner appropriate to the disease and/or neurological conditions and/or nervous system damage to be treated as determined by persons skilled in the medical arts. In addition, suitable duration and frequency of administration of the plasticity-modifying agent may also be determined or adjusted by such factors as the condition of the patient, the type and severity of the patient's disease, the particular form of the active ingredient, and the method of administration. Optimal doses of the plasticity-modifying agent may generally be determined using experimental models and/or clinical trials. The optimal dose may depend upon the body mass, weight, or blood volume of the subject. The use of the minimum dose that is sufficient to provide effective therapy is usually preferred. Design and execution of pre-clinical and clinical studies for a plasticity-modifying agent described herein are well within the skill of a person skilled in the relevant art.

For the treatment of neurodegenerative diseases, the plasticity-modifying agent may be administered locally, in particular by injection or infusion into the targeted cerebral area. It can also be administered using a controlled-release device, for example an osmotic minipump connected to a canula implanted in the brain.

All of the above cited disclosures of patents, publications and database entries are specifically incorporated herein by reference in their entirety to the same extent as if each such individual patent, publication or entry were specifically and individually indicated to be incorporated by reference.

In addition to the above arrangements, the invention also comprises other arrangements, which will emerge from the description, which refers to exemplary embodiments, with reference to the Figures in which:

FIG. 1. Ligands interact with Otx2. (a) Example dot blot (DB) of biotinylated sulfopeptides incubated or not with Otx2 protein. (b) Quantification of DB chemiluminescence with at least 3 duplicate experiments per data point.

Figure 2:
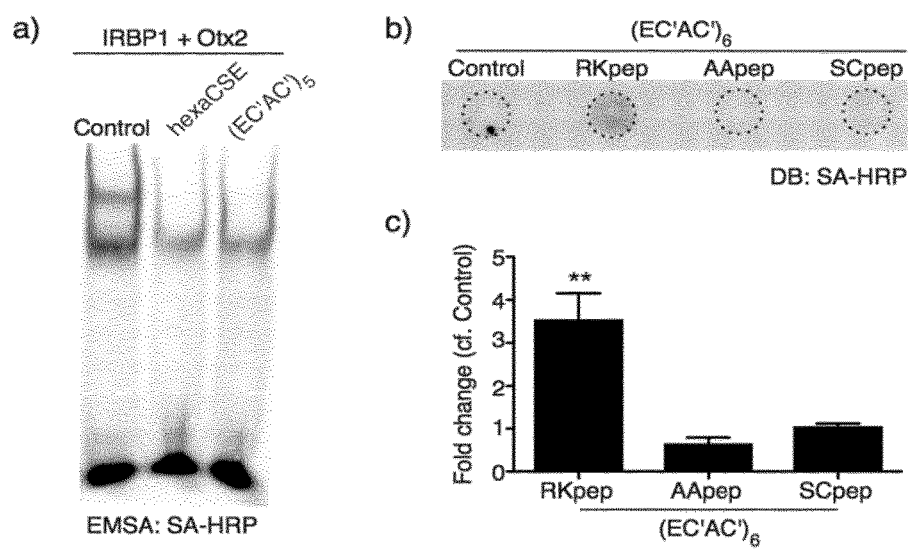

FIG. 2. Ligands interact with the GAG-binding site of Otx2. (a) Electrophoretic mobility shift assay (EMSA) with biotinylated IRBP1 DNA probe and Otx2 protein shows loss of shift when incubated with hexaCSE and (EC'AC')$_5$. (b) Dot blot (DB) of (EC'AC')$_6$ incubated with GAG motif peptide (RKpep) or control peptides (AApep, SCpep). (c) Quantification of DBs. All values: N=3; mean±SEM; one-way ANOVA with Bonferonni posthoc test; **$P<0.01$.

Figure 3:
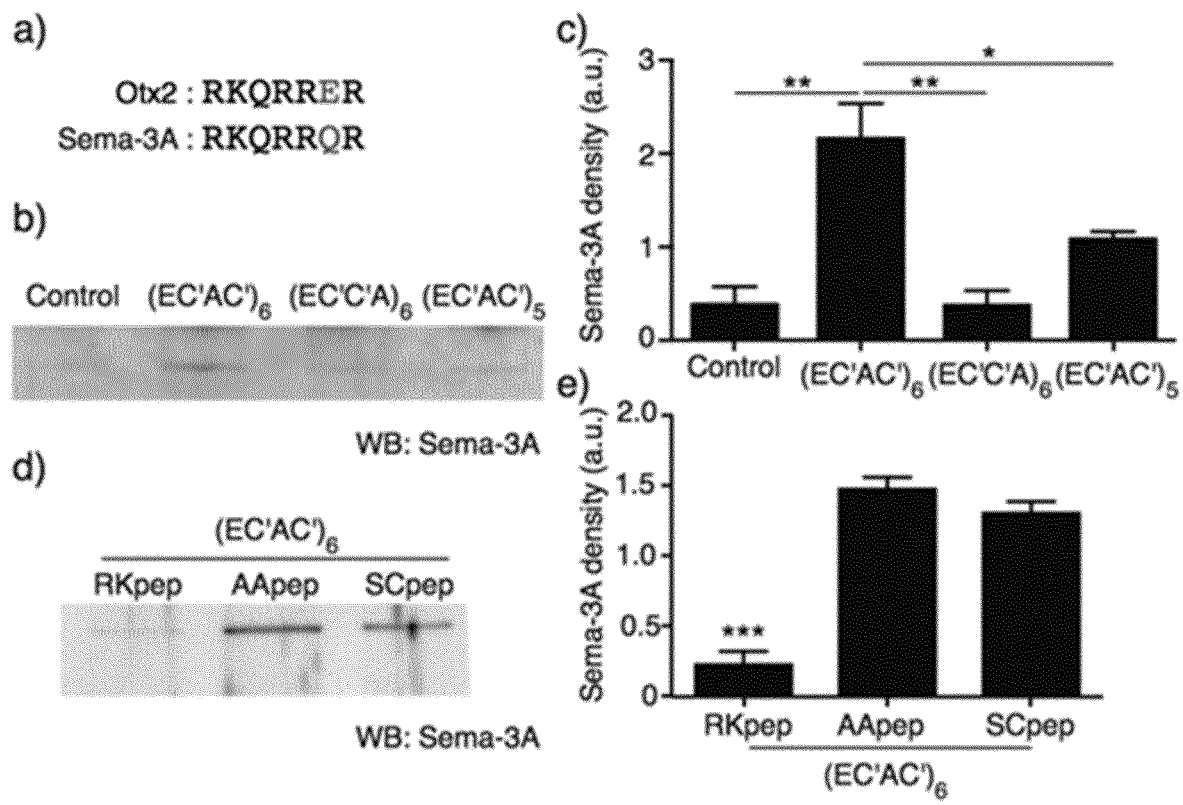

FIG. 3. Ligand pull-down experiments with lysates of adult mouse visual cortex. (a) Comparison of GAG-binding motifs. (b) Western blot (WB) for Sema-3A after pull-down with ligands retained on streptavidin beads (Control is beads alone). (c) Quantification of WBs. (d) WB for Sema-3A after pull-down with (EC'AC')$_6$ incubated with GAG motif peptide (RKpep) or control peptides (AApep, SCpep). (e) Quantification of WBs. All values: N=3; mean±SEM; one-way ANOVA with Bonferonni posthoc test; *$P<0.05$, $P<0.01$, *$P<0.001$.

Figure 4:
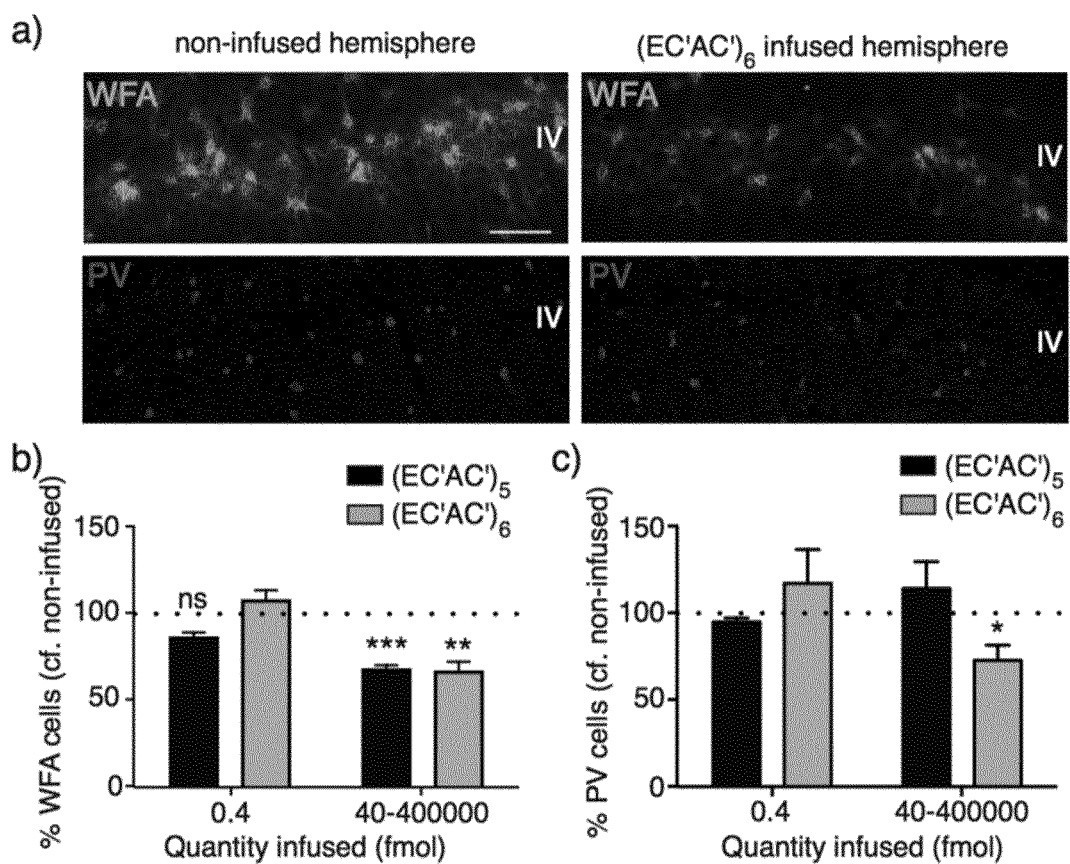

FIG. 4. Ligands have in vivo activity. (a) Representative images of staining for *Wisteria floribunda* agglutinin (WFA), which labels PNNs, and parvalbumin (PV) in adult mouse primary visual cortex layer IV infused or not with 40 fmol (EC'AC')$_6$. (b) Quantification of WFA+ cell numbers. (c) Quantification of PV cell numbers. Scale bar=100 μm. All values: N=3-6; mean±SEM; t-test; *$P<0.05$, $P<0.01$, *$P<0.001$.

Figure 5:
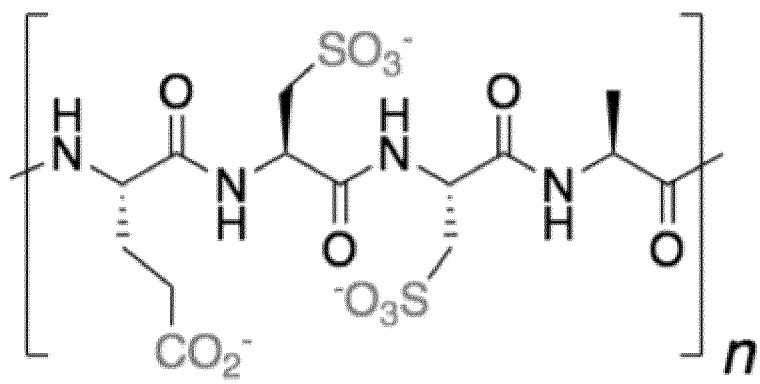
Figure 5:
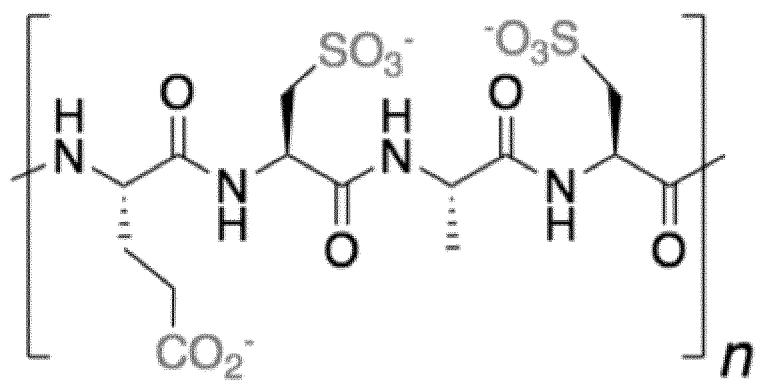

FIG. 5. GAG mimics peptide scaffold of the invention: EC'C'A and EC'AC', where C' represents cysteic acid.

EXAMPLE

Materials and Methods

Compounds

The sequences (ECCA)n and (ECAC)n (n=3-6) were synthesized by Fmoc strategy on a Rink amide MBHA resin. A 6-aminohexanoic acid (Ahx) spacer was introduced at the N-terminus and the peptidyl resins were either acetylated (Ac) or acylated with a biotin sulfone (Biot(SO2)). The peptides were cleaved from the resin by TFA and precipitated in diethyl ether to give either Ac-Ahx-(ECAC)n-NH2, Ac-Ahx-(ECCA)n-NH2, Biot(S02)-Ahx-(ECAC)n-NH2, or Biot(S02)-Ahx-(ECCA)n-NH2. These precursors were oxidized with performic acid to give cysteic acid (C') peptides, then neutralized with aqueous ammonia resulting in GAG mimics (EC'AC')n and (EC'C'A)n, with either an acetyl or a biotin sulfone at the N-terminus and an amide at the C-terminus. Crude sulfopeptides were desalted on Sephadex G25, purified by reverse phase HPLC and characterized by mass spectroscopy. These GAG mimic peptides can be stored for months at −20° C. as sodium salts.

Dot Blots

For competition assays, 400 pmol of biotinylated ligand or hexaCSE were incubated 30 min at 37° C. in 100 mM ammonium acetate with 1 μg of Otx2 protein (in-house) and with 3 μg of RK-, AA- or SC-peptide. Each solution was then spotted on a nitrocellulose membrane and biotin was detected by 30-min incubation with streptavidin-HRP (ThermoFisher Scientific) followed by chemiluminescence (#34580, ThermoFisher Scientific) reaction. Membranes were digitized with an LAS-4000 (Fujifilm) and quantified by densitometry with ImageJ.

Gel Shift

Otx2 protein (0.1 μg) was incubated at room temperature for 30 min with 40 fmol of biotinylated IRBP1 oligonucleotide and 4 pmol of (EC'AC')$_5$ or hexaCSE in 50 ng/μl dIdC, PBS. Samples were separated on 6% native polyacrylamide gels at 100 V in TBE then transferred onto a nylon membrane at 380 mA for 45 min, crosslinked with UV (120,000 μJ/cm$^2$, Amersham). The LightShift Chemiluminescent EMSA Kit (#89880, ThermoFisher Scientific) was used for detection and membranes were digitized with an LAS-4000 (Fujifilm) and quantified by densitometry with ImageJ.

Immunoprecipitation

Visual cortex of adult mice were dissected and lysed in homogenization buffer (0.32 M sucrose, 5 mM HEPES, 10 mM MgCl$_2$ and protease inhibitors). Samples were centrifuged (8 min, 1700 g) at 4° C. and the supernatant was incubated 2 hours at 37° C. with 5 nmol of GAG mimics. For the competition assay, ligands were pre-incubated 30 min with 50 nmol of RK-, AA- or SC-peptide at 37° C. prior to incubation overnight at 4° C. with streptavidin-coupled Dynabeads (Life technologies). The loaded beads were washed with homogenization buffer and heated 10 min at 95° C. in Laemmli buffer (with DTT) to detach proteins for western blot analysis.

Western Blot

Immunoprecipitated proteins were separated on NuPAGE 4-12% Bis-Tris pre-cast gels (Invitrogen) for 1 h at 200 V and transferred onto a methanol-activated PVDF membrane at 400 mA for 1 h. Membranes were blocked with 5% non-fat dry milk for 1 h before incubation with primary antibody anti-Sema3A (rabbit, 1/1000, Millipore) overnight at 4° C. Membranes were washed and incubated 1 h with secondary antibody anti-rabbit HRP-linked (Cell Signaling). Membranes were digitized with an LAS-4000 (Fujifilm) and quantified by densitometry with ImageJ.

Brain Infusions and Immunohistochemistry

Three-month-old C57BL/6J mice (Janvier) were infused for 7 days into V1 (lambda: x=1.7 mm, y=0 mm, z=0.5 mm) with various concentrations of ligands (4 pM, 400 pM or 4 μM), using Alzet micro-osmotic pumps (0.5 μL/h). Animals were then perfused with PBS and 4% paraformaldehyde. Cryostat sections (20 μm) were incubated overnight with primary antibody anti-parvalbumin (rabbit, 1/500, Swant) and WFA-FITC (1/100, Vector), followed by secondary antibody anti-rabbit Alexa Fluor-546 (1/2000, Molecular Probes) for 1 h. Images were acquired with a Leica SP5 confocal microscope and quantified by analysis with ImageJ.

Statistical Analysis

Analysis was performed with Prism 6 (GraphPad). Single comparisons were made by t-test, whereas multiple group analyses were made by ANOVA followed by Bonferonni's posthoc test.

Results

To evaluate affinity of the biotinylated (EC'C'A)$_n$ and (EC'AC')$_n$ libraries to Otx2 protein, we performed dot blots with nitrocellulose membranes for which sulfopeptide retention requires interaction with protein (FIG. 1a). While Otx2 binding did not favor one motif over the other, there was a clear increase in affinity as a function of n repeats (FIG. 1b). For comparison, dot blots were performed with hexaCSE, which was previously shown to bind Otx2 and interfere with its in vivo activity in the mouse brain. Sequences with n=4 or 5 repeats were found to bind to Otx2 equally as well as hexaCSE, while those with n=6 where found to bind 2- to 3-fold better.

To confirm the biotinylated ligands interact with Otx2 through its previously identified GAG-binding site, we performed DNA chase and peptide binding experiments (FIG. 2). In Otx2, a GAG-binding motif is located in the first helix of its DNA-binding domain, thus specific binding of GAG molecules may interfere with DNA binding. Assays show the (EC'AC')$_5$ mimic is able to chase the IRBP1 DNA probe from Otx2 to the same extent as biotinylated hexaCSE positive control (FIG. 2a). The GAG-binding site in Otx2 (RKQRRER) contains an arginine-lysine doublet (RK) which when mutated to an alanine doublet (AA), no longer binds ECM and causes critical period defects in the Otx2$^{+/AA}$ mouse model. Dot blot assays with peptides (15-mer) based on this motif were used to assess whether (EC'AC')$_6$ binds specifically (FIG. 2b). While the wild type peptide (RKpep: RKQRRERTTFTRAQL) retained the ligand, the mutated peptide (AApep: AAQRRERTTFTRAQL) did not; neither did a scrambled peptide (SCpep: RTQTRFRTRARLEQK) containing the same residues as the RKpep but in random order (FIG. 2c). These assays confirm the interaction is not simply electrostatic but requires a specific residue sequence.

To measure the in vivo activity and specificity of biotinylated GAG mimics, we performed biochemical and immunohistochemical analyses. Otx2 and Semaphorin-3A (Sema-3A) are both keys actors of visual cortex plasticity and share a similar motif for binding CS-E (FIG. 3a). We first focused on Sema-3A, as cortical Otx2 levels are too low to be reliably detected biochemically. By using ligands in pull-down experiments with lysates of adult mouse visual cortex, we found that (EC'AC')$_5$ and (EC'AC')$_6$ but not (EC'C'A)$_6$ interact with Sema-3A (FIG. 3b-c). The RKpep specifically disrupts Sema-3A interaction with (EC'AC')$_6$ in these lysates (FIG. 3d-e), suggesting involvement of Sema-3A GAG-binding motif.

After 7-day infusion of either (EC'AC')$_5$ or (EC'AC')$_6$ in adult mouse visual cortex, 40 fmol caused a reduction in PNN assembly (FIG. 4a-b). Infusion with up to 10$^5$-fold more of either mimic provided the same reduction. A feedback loop exists between Otx2 accumulation in PV cells and assembly of surrounding PNNs; PNNs attract extracellular Otx2 while Otx2 activity in PV cells increases PNN expression. These results suggest that these ligands interfere with Otx2 signaling enough to break this feedback loop and diminish PNN assembly. Furthermore, interfering with Otx2 signaling in the adult visual cortex has been shown to reverse PV cell maturation state and induce plasticity. Here, only infusion of (EC'AC')$_6$ (>40 fmol) resulted in significantly reduced PV expression (FIG. 4c). This modest reduction (>25%) has been previously shown to be sufficient for re-opening brain plasticity.

These pull-down and infusion experiments confirm in vitro findings that the longer ligands have higher affinity for GAG-binding proteins; only when n=6 for the (EC'AC')$_n$ mimic do we observe full effects on PV cell maturation (FIG. 4c). They also suggest that (EC'AC')$_n$ and (EC'C'A)$_n$ mimics can provide specificity and selectivity. While Otx2 shows no preference for either motif in vitro (FIG. 1b), Sema-3A interacts with the (EC'AC')$_n$ motif but not the (EC'C'A)$_n$ motif in brain lysates (FIG. 3c). Thus, these GAG mimics contain valid electrostatic patterns to recapitulate specific sulfation patterns present in natural GAGs.

The invention claimed is:

1. A ligand, or any of its pharmaceutically acceptable salts, said ligand comprising or consisting of a polypeptide of the general formula (I):

[X]n     (I)

wherein
  n is comprised between 3 and 50,
  X is a peptide comprising from 4 to 6 amino acids,
  X comprises an amino acid selected from the group consisting of glutamic acid and aspartic acid,
  X comprises one or two cysteic acid (s), and
  X comprises at least one neutral amino acid other than cysteine,
  wherein said ligand is able to interact with binding of one effector molecule with at least one glycosaminoglycan (GAG).

2. The ligand according to claim 1, characterized in that n is comprised between 3 and 35.

3. The ligand according to claim 1, characterized in that X comprises two cysteic acids.

4. The ligand according to claim 1, characterized in that X comprises two homocysteic acids.

5. The ligand according to claim 1, characterized in that the at least one neutral amino acid other than cysteine is chosen from the group consisting of alanine, asparagine, glutamine, histidine, isoleucine, methionine, phenylalanine, proline, serine, threonine, tryptophan, tyrosine, valine, and 2-aminoisobutyric acid.

6. The ligand according to claim 1, characterized in that the neutral amino acid other than cysteine is alanine.

7. The ligand according to claim 1, characterized in that the amino acid selected from the group consisting of glutamic acid and aspartic acid is placed in the first position of peptide X starting from the C-terminus.

8. The ligand according to claim 1, characterized in that X in polypeptide [X]$_n$ is selected in the group consisting of EACC, ECCA and ECAC, with C is cysteic acid, A is alanine, E is glutamic acid.

9. The ligand according to claim 1, characterized in that the ligand is able to interact with a glycosaminoglycan (GAG) binding site.

10. The ligand according to claim 9, characterized in that the said glycosaminoglycan GAG is selected from the group consisting of heparan sulfate, heparin and chondroitin sulfate.

11. The ligand according to claim 1, characterized in that the ligand is able to prevent the binding of at least one effector molecule with at least one glycosaminoglycan (GAG).

12. The ligand according to claim 11, characterized in that the said effector molecule is selected from the group consisting of transcription factors, growth factors, signaling factors, coagulation cascade proteins, an effector molecule chosen from the group consisting of Semaphorins, and homeoprotein family.

13. The method of administering a medicament to a subject, comprising administering the ligand according to claim 1 to a subject in need thereof.

14. A method of treating a disease and/or neurological conditions and/or nervous system damage, comprising administering the ligand according to claim 1 to a subject in need thereof,
  wherein the disease and/or neurological conditions and/or nervous system damage is selected from the group consisting of:
    nervous system damage following cerebrovascular accident, ischemic, hemorrhagic, neoplastic, degenerative, traumatic, and/or neurodevelopmental damage;
    nervous system damage following events;
    neurodegenerative diseases;
    conditions caused by nutrient deprivation or toxins;
    neurodevelopmental diseases;
    neuropsychiatric diseases;
    depression, epilepsy; and
    degenerative diseases affecting the eyes or ears.

15. A pharmaceutical composition comprising the ligand according to claim 1.

16. The ligand according to claim 1, wherein n is comprised between 3 and 15.

17. The ligand according to claim 1, wherein n is comprised between 3 and 6.

18. The ligand according to claim 11, wherein said effector molecule is selected from Semaphorins and homeoprotein family.

19. The ligand according to claim 11, wherein said effector molecule is Otx2 or Semaphorin-3A.

20. The method according to claim 14, wherein:
  the nervous system damage follows a stroke or an injury;
  the neurodegenerative disease is selected from the group consisting of multiple sclerosis, amyotrophic lateral sclerosis, subacute sclerosing panencephalitis, Parkinson's disease, Huntington's disease, muscular dystrophy, Alzheimer's disease, idiopathic dystonia, Spinal muscular atrophy or Wilson's disease;
  the neurodevelopmental disease is an autism or a dyslexia;
  the neuropsychiatric disease is a schizophrenia or a bipolar disorder, and
  the degenerative disease affecting the eyes or ears is a glaucoma or an amblyopia.

* * * * *